United States Patent [19]

Nguyen

[11] Patent Number: 5,092,919

[45] Date of Patent: Mar. 3, 1992

[54] CERTAIN 2-(2'METHYL-3',4'-TRISUBSTITUTED BENZOYL)-1,3-CYCLOHEXANEDIONES

[75] Inventor: Nhan H. Nguyen, Hercules, Calif.

[73] Assignee: Imperial Chemical Industries plc, London, England

[21] Appl. No.: 641,200

[22] Filed: Jan. 15, 1991

[51] Int. Cl.$^5$ ............................................. A01N 35/06
[52] U.S. Cl. ................................. 71/122; 71/98; 71/103; 568/329; 568/306; 568/31; 568/43
[58] Field of Search ................ 568/31, 43, 306, 329; 71/98, 103, 122, 123

[56] References Cited

U.S. PATENT DOCUMENTS

| | | | |
|---|---|---|---|
| 4,762,551 | 8/1988 | Knudsen | 568/43 |
| 4,781,751 | 11/1988 | Chin | 71/103 |
| 4,783,213 | 11/1988 | Lee | 568/329 |
| 4,853,028 | 8/1989 | Carter et al. | 568/43 |
| 4,918,236 | 4/1990 | Knudsen et al. | 568/329 |
| 4,954,165 | 9/1990 | Baba et al. | 568/329 |
| 4,957,538 | 9/1990 | Michaely | 568/329 |
| 4,997,473 | 3/1991 | Nguyen | 568/31 |
| 5,006,158 | 4/1991 | Carter et al. | |

FOREIGN PATENT DOCUMENTS

| | | | |
|---|---|---|---|
| 0186120 | 12/1985 | European Pat. Off. | 71/98 |
| 252298 | 1/1988 | European Pat. Off. | 568/329 |
| 317158 | 5/1989 | European Pat. Off. | 568/329 |
| 318075 | 6/1989 | European Pat. Off. | 568/329 |

Primary Examiner—James H. Reamer
Attorney, Agent, or Firm—Edwin H. Baker

[57] ABSTRACT

Herbicidal compounds of the structural formula

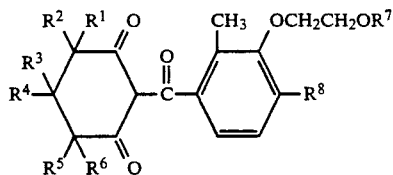

wherein $R^1$ is hydrogen or $C_1$-$C_4$ alkyl; $R^2$ is hydrogen or $C_1$-$C_4$ alkyl; $R^3$ is hydrogen or $C_1$-$C_4$ alkyl; $R_4$ is hydroxy, hydrogen or $C_1$-$C_4$ alkyl; or $R^3$ and $R^4$ together are carbonyl (=O) with the proviso that $R^1$, $R^2$, $R^5$ and $R^6$ are $C_1$-$C_4$ alkyl; $R^5$ is hydrogen or $C_1$-$C_4$ alkyl; $R^6$ is hydrogen, $C_1$-$C_4$ alkyl, $C_1$-$C_4$ alkylthio, or $C_1$-$C_4$ alkylsulfonyl, with the proviso that when $R^6$ is $C_1$-$C_4$ alkylthio or $C_1$-$C_4$ alkylsulfonyl, the $R_3$ and $R^4$ are not together carbonyl; $R^7$ is methyl or ethyl; and $R^8$ is (1) halogen; (2) nitro; or (3) $R^bSO_n$— wherein n is the integer 0 or 2, and $R^b$ is (a) $C_1$-$C_4$ alkyl; and its salts.

12 Claims, No Drawings

CERTAIN 2-(2'METHYL-3',4'-TRISUBSTITUTED BENZOYL)-1,3-CYCLOHEXANEDIONES

BACKGROUND OF THE INVENTION

European Patent Publication No. 0,186,120 was published on July 2, 1986, and relates to certain prior art 2-(2'-methyl-3,4 substituted benzoyl)-1,3-cyclohexane-1,3-diones as herbicides. The compounds can have the following structural formula

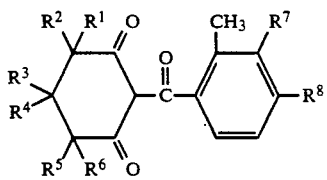

wherein $R^1$ through $R^8$ are substantially the same as defined below except that $R^7$ can be alkoxy or trifluoromethoxy.

The compounds of the present invention have unexpectedly superior herbicidal activity over the cited prior art compounds or give unexpectedly reduced injury to certain crop plants.

DESCRIPTION OF THE INVENTION

This invention relates to 2-(2' methy, 3',4'-tri-substituted benzoyl)-1,3-cyclohexanediones, their use as herbicides and herbicidal compositions containing the compounds.

Embodied within the scope of this invention are novel compounds having the following structural formula

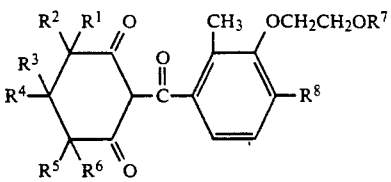

wherein
$R^1$ is hydrogen or $C_1$-$C_4$ alkyl, preferably methyl;
$R^2$ is hydrogen or $C_1$-$C_4$ alkyl, preferably methyl;
$R^3$ is hydrogen or $C_1$-$C_4$ alkyl, preferably methyl;
$R_4$ is hydroxy, hydrogen or $C_1$-$C_4$ alkyl, preferably methyl; or
$R^3$ and $R^4$ together are carbonyl (=O) with the proviso that $R^1$, $R^2$, $R^5$ and $R^6$ are $C_1$-$C_4$ alkyl, preferably all methyl;
$R^5$ is hydrogen or $C_1$-$C_4$ alkyl, preferably methyl;
$R^6$ is hydrogen, $C_1$-$C_4$ alkyl, preferably methyl, $C_1$-$C_4$ alkylthio, preferably methylthio or $C_1$-$C_4$ alkylsulfonyl, preferably methylsulfonyl, with the proviso that when $R^6$ is $C_1$-$C_4$ alkylthio or $C_1$-$C_4$ alkylsulfonyl, then $R^3$ and $R^4$ are not together carbonyl;
$R^7$ is methyl or ethyl; and
$R^8$ is (1) halogen, preferably chlorine or bromine; (2) nitro; or (3) $R^bSO_n$— wherein n is the integer 0 or 2, preferably 2, and $R^b$ is (a) $C_1$-$C_4$ alkyl, preferably methyl or ethyl.

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine.

Salts of the above-described compounds (as defined hereinafter) are also the subject of the instant invention.

The compounds of this invention can have the following four structural formulae because of tautomerism:

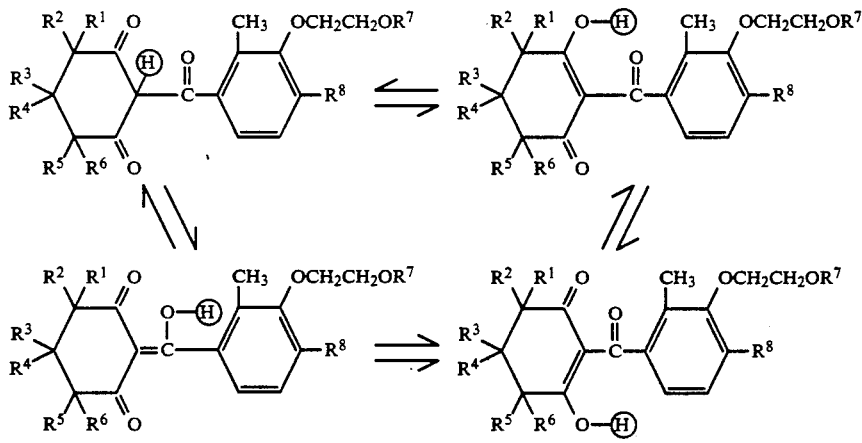

wherein $R^1$, $R^2$, $R^3$, $R^4$, $R^5$, $R^6$, $R^7$ and $R^8$ are as defined above.

The circled proton on each of the four tautomers is reasonably labile. These protons are acidic and can be removed by any base to give a salt having an anion of the following four resonance forms:

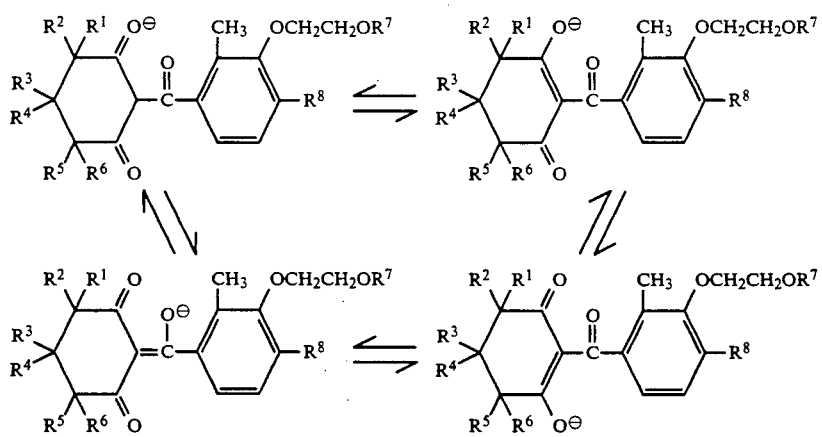

wherein $R^1$, $R^2$, $R^3$, $R^4$, $R^5$, $R^6$, $R^7$, and $R^8$ are as defined above.

Examples of cations of these bases are inorganic cations such as alkali metals e.g. lithium, sodium, and potassium or organic cations such as substituted ammonium, sulfonium or phosphonium wherein the substituent is an aliphatic or aromatic group.

The compounds of this invention and their salts are active herbicides of a general type. That is, they are herbicidally effective against a wide range of plant species. the method of controlling undesirable vegetation of the present invention comprises applying an herbicidally effective amount of the above-described compounds to the area where control is desired.

The compounds of the present invention can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

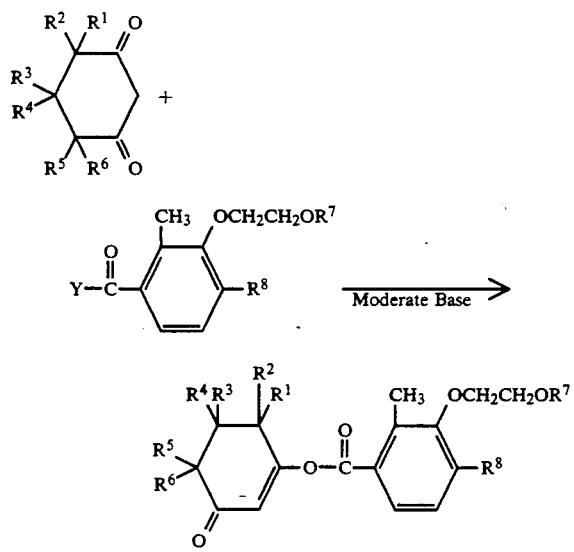

wherein $R^1$ through $R^8$ are as defined and Y is halogen, preferably chlorine, $C_1$-$C_4$ alkyl—C(O)—O—, $C_1$-$C_4$ alkoxy-C(O)—O— or

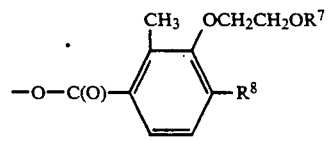

wherein $R^7$ and $R^8$ in this portion of the molecule are identical with those in the reactant shown above and the moderate base is as defined, preferably tri-$C_1$-$C_6$ alkylamine, pyridine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably are added to the reaction mixture with cooling. The mixture is stirred at 0° C.-50° C. until the reaction is substantially complete.

The reaction product is worked up by conventional techniques.

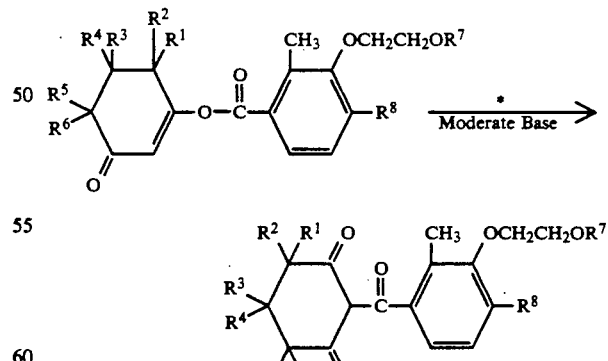

\* = Cyanide source.
Moderate base = as defined herein
wherein $R^1$ through $R^8$ are as defined.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1-10 mole percent of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature acid chloride or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis*, Vol I, L. G. Fieser and M. Fieser, pp. 767-769 (1967).

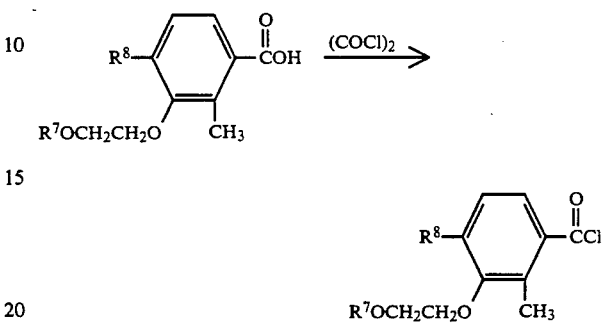

wherein $R^7$ and $R^8$ are as previously defined.

The above-described 5-hydroxy-4,4,6,6-tetra-substituted 1,3-cyclohexanediones can be prepared according to the following reaction.

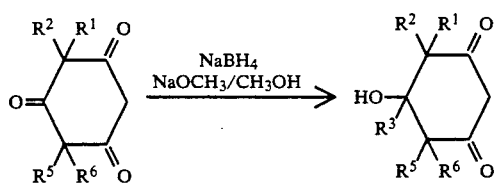

wherein $R^1$, $R^2$, $R^5$, and $R^6$ are as defined and $R^3$ is hydrogen.

In this reaction NaBH$_4$ is added to a basic methanolic solution of the syncarpic acid under controlled conditions and reacted at room temperature. The reaction solution is acidified and the product recovered by conventional techniques.

When $R^3$ is $C_1$-$C_4$ alkyl, the dione can be prepared by reacting a nucleophile such as methyl lithium with a 4,4,6,6-tetra-substituted 1,3,5-cyclohexanetrione as displayed in the following reaction.

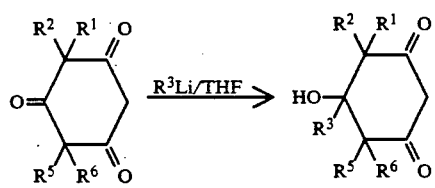

wherein $R^1$, $R^2$, $R^5$ and $R^6$ are as defined and $R^3$ is $C_1$-$C_4$ alkyl.

In this reaction the lithium compound is added to a solution of the syncarpic acid reactant under controlled conditions and reacted at room temperature. The reaction solution is then acidified and the product recovered by conventional techniques.

The substituted 1,3-cyclohexandiones of the formula

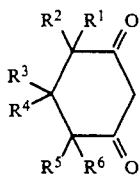

where $R^1$ through $R^5$ are as defined and $R^6$ is $C_1$–$C_4$ alkylthio or $C_1$–$C_4$ alkylsulfonyl can be prepared by a wide variety of general methods according to the teachings of *Modern Synthetic Reactions*, 2nd Edition, Chapter 9, H. O. House, W. A. Benjamin, Inc., Menlo Park, CA (972).

The trisubstituted benzoic acid chloride intermediates can prepared by the following general method as shown in the Figure of the next page wherein R is $C_1$–$C_4$ alkyl, $R_1$ is —$CH_2CH_2OCH_3$ or —$CH_2CH_2OC_2H_5$, $R^2$ is $C_1$–$C_4$ alkyl and X is halogen, preferably chlorine or bromine.

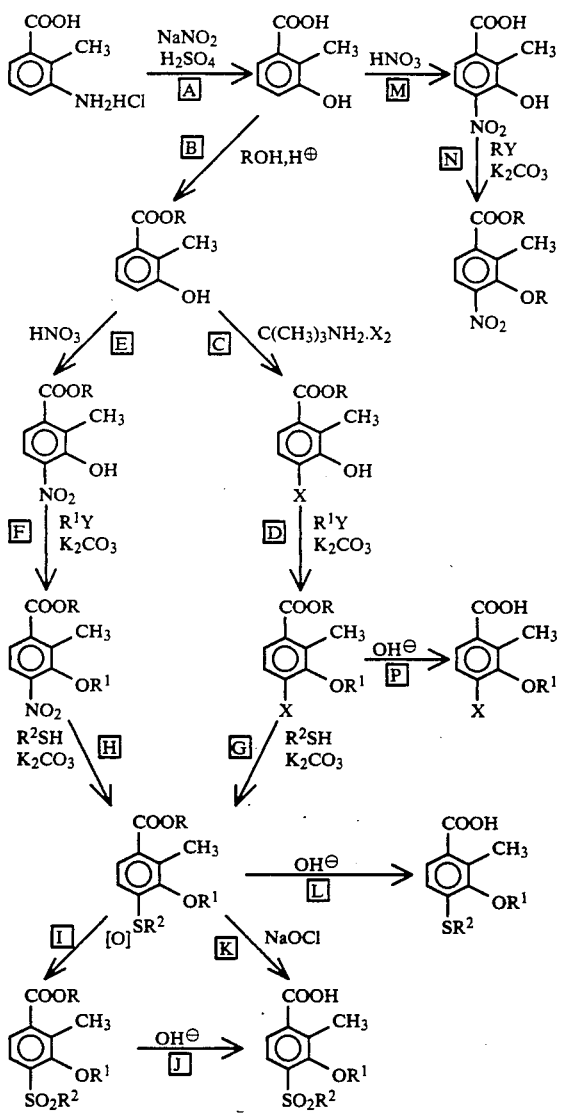

Referring to the Figure, and particularly to Reaction Steps (A) through (J) consider the following:

Generally in Reaction Step (A), a mole amount of anilinium hydrochloride is reacted slowly with a slight mole excess of sodium nitrate and a mole excess of sulfuric acid. The reaction temperature is maintained at about 0° to 15° C. until a solution is obtained. The solution slowly is added to a heated aqueous solution of sulfuric acid and heated to reflux. A solid reaction product is recovered and purified by conventional techniques.

For Reaction Step (B), 2-methyl-3-hydroxy benzoic acid is reacted with a $C_1$–$C_4$ alcohol with concentrated sulfuric acid at reflux temperatures. The reaction product is recovered and purified by conventional techniques.

For Reaction Step (C), a mole amount of a $C_1$–$C_4$ alkyl ester of 2-methyl-3-hydroxy benzoic acid is reacted with a mole amount of a tertiary butyl amine and a mole of bromine or chlorine in a solvent such as methylene chloride at temperatures from —50° C. to room temperature.

For Reaction Step (D), a mole amount of a $C_1$–$C_4$ alkyl ester of 2-methyl-3-hydroxy-4-bromobenzoic acid is alkylated with a mole amount of the requisite alkylating agent such as a $C_1$–$C_4$ alkyl iodide or chloride or a di-$C_1$–$C_4$ alkyl sulfate and a mole amount of a base such as potassium carbonate in a solvent such as a mixture of acetone and dimethyformamidine (DMF). The reaction can be run at reflux temperatures and the reaction product recovered by conventional techniques.

For Reaction Step (E), a mole amount of a $C_1$–$C_4$ alkyl ester of 2-methyl-3-hydroxy benzoic acid is reacted with at least two mole of nitric acid in glacial acetic acid. The reaction can be run at room temperature. The reaction product is recovered by conventional techniques.

For Reaction Step (F) is carried out by reacting a mole of a $C_1$–$C_4$ alkyl ester of 2-methyl-3-hydroxy-4-nitro-benzoic acid with a mole amount of the requisite alkylating agent such as $C_1$–$C_4$ alkyl chloride or iodide or a di-$C_1$–$C_4$ alkyl sulfate and a mole amount of a base such as potassium carbonate in a solvent such as a mixture of acetone and DMF. The reaction can be run at reflux temperatures and the reaction product recovered by conventional techniques.

For Reaction Step (G) is carried out by reacting a mole amount of a $C_1$–$C_4$ alkyl ester of 2-methyl-3-($C_1$–$C_4$ alkoxy, $C_1$–$C_4$ haloalkoxy 2-methoxyethoxy or 2-ethoxyethoxy)-4-bromobenzoic acid with a mole amount of a $C_1$–$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product recovered by conventional techniques.

Reaction Step (G) can also be rerun by reacting a mole amount of a $C_1$–$C_4$ alkyl ester of 2-methyl-3-($C_1$–$C_4$ alkoxy, $C_1$–$C_4$ haloalkoxy 2-methoxyethoxy, or 2-ethoxyethoxy)-4-bromobenzoic acid with a mole amount of a $C_1$–$C_4$ alkylthioglycolate according to the teaching of U.S. patent application Ser. No. 07/590,115, filed Sept. 28, 1990, and entitled "Improved Method For The Preparation of 4-Methylsulfonyl Benzoic Acid Derivatives and Intermediates", incorporated herein by reference.

For Reaction Step (H) is run by reacting a mole amount of a $C_1$–$C_4$ alkyl ester of 2-methyl-3-($C_1$–$C_4$ alkoxy, $C_1$–$C_4$ haloalkoxy 2-methoxyethoxy or 2-ethoxyethoxy)-4-nitro-benzoic acid with mole amount of a $C_1$-$C_4$ alkyl mercaptan benzoic acid with a mole amount of a $C_1$-$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product recovered by conventional techniques.

Reaction Step (H) can also be rerun by reacting a mole amount of a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-nitrobenzoic acid with a mole amount of a $C_1$-$C_4$ alkyl-thioglycolate according to the teaching of U.S. patent application Ser. No. 07/590,115, filed Sept. 28, 1990, and entitled "Improved Method For The Preparation of 4-Methylsulfonyl Benzoic Acid Derivatives and Intermediates", incorporated herein by reference.

For Reaction Step (I) is carried out by reacting a mole amount of a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-($C_1$-$C_4$ alkylthio)benzoic acid with at least 3 mole of an oxidizing agent such as acetyl peroxyacid or m-chloroper-benzoic acid in a suitable solvent such as methylene chloride by stirring a solution of the reactants at 20° to 40° C. The desired reaction product is recovered by conventional techniques. During this reaction step the $C_1$-$C_4$ alkylthio substituent is oxidized to the corresponding $C_1$-$C_4$ alkylsulfonyl substituent without hydrolysis of the ester group to an acid group.

For Reaction Step (J), a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-($C_1$-$C_4$ alkylsulfonyl)benzoic acid is hydrolized to the corresponding trisubstituted benzoic acid by reaction with a mole amount of sodium hydroxide in an aqueous medium. The hydrolysis is run at a temperature of between 20° to 100° C. with stirring. The reaction product is recovered by conventional techniques.

For Reaction Step (K) is run by reacting a mole amount of a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-($C_1$-$C_4$ alkylthio)benzoic acid with at least 5 mole of an oxidizing agent such as sodium hypochlorite in a suitable solvent such as dioxane by heating a solution of the reactants at a temperature of 60° to 80° C. After an exothermic reaction the mixture is cooled and acidified with hydrochloric acid. The desired trisubstituted benzoic acid intermediate is a precipitate an is recovered by filtration.

For Reaction Step (L), a mole amount of a $C_1$-$C_4$ alkyl ester of 2-methyl-3-($C_1$-$C_4$ alkoxy, $C_1$-$C_4$ haloalkoxy 2-methoxyethoxy or 2-ethoxyethoxy)-4-($C_1$-$C_4$ alkylthio)benzoic acid is hydrolyzed with a base such as sodium hydroxide to the corresponding 2-methyl-3-($C_1$-$C_4$ alkoxy or $C_1$-$C_4$ haloalkoxy)-4-($C_1$-$C_4$ alkylthio)benzoic acid. The hydrolysis is run in a solvent such as an 89 percent methanol-water mixture. The reaction can be run at 25° to 100° C. with stirring the desired reaction product is recovered by conventional techniques.

For Reaction Step (M), a mole amount of 2-methyl-3-hydroxy benzoic acid is reacted with at least 2 mole of nitric acid in a solvent such as glacial acetic acid. The reaction can be run at room temperature and the reaction product recovered by conventional techniques.

For Reaction Step (N), 2-methyl-3-hydroxy-4-nitrobenzoic acid is needed with 2 mole of $C_1$-$C_4$ alkyl iodide or $C_1$-$C_4$ alkyl chloride and 2 mole of a base such as potassium carbonate in a solvent such as a mixture of acetone and DMF. The reaction can be run at reflux temperatures and the reaction product is recovered by conventional techniques.

The reaction product is the $C_1$-$C_4$ alkyl ester of 2-methyl-3-($C_1$-$C_4$ alkoxy)-4-nitrobenzoic acid. The $C_1$-$C_4$ alkyl groups will be identical. The reaction product is useful per se as an intermediate or can be used as a reactant in Reaction Step (H)-(L) described hereinafter.

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as methylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours. These acid chlorides can be reacted with the above-described 1,3-cyclohexanedione to prepare the above-described herbicidal 2,3,4-trisubstituted benzoyl-1,3-cyclohexanediones according to the following two-step reaction.

The trisubstituted benzoic acid chloride intermediates are useful in the preparation of the previously described herbicidal 2-(2',3',4'-trisubstituted benzoyl)-1,3-cyclohexanediones.

The following series of examples teach the synthesis of representative intermediate compounds of this invention. The structures of all compounds of the examples and tables were verified by nuclear magnetic resonance (NMR), infrared spectroscopy (IR) and mass spectroscopy (MS).

EXAMPLE I 3-hydroxy-2-methylbenzoic acid

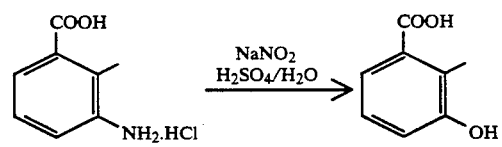

To a suspension of the anilinium hydrochloride salt (12.5 grams (g), 0.067 mol) in $H_2O$/ice/concentrated $H_2SO_4$ (60 milliliters (ml)/37 g/ 37 ml) was added a solution of $NaNO_2$ (4.76 g, 0.069 mol) in $H_2O$ (12 ml) slowly over 5 minutes. The reaction temperature was maintained at 5° C. with external cooling by an ice bath. The solid went into solution and the yellow solution was stirred for another 5 minutes. The solution was transferred to an addition funnel and added dropwise over 25 minutes to a heated solution of concentrated $H_2SO_4/H_2O$ (44 ml/34 ml). The reaction mixture was heated at reflux for another 5 minutes, cooled to room temperature, then immersed in an ice bath. The precipitate formed was collected by suction filtration and dissolved in ethylacetate (EtOAc). The mother liquor was extracted twice with EtOAc. The combined EtOAc layers were dried over magnesium sulfate ($MgSO_4$), filtered, and concentrated to a yellow solid (10.0 g, 0.065 mol, 97 percent yield). The structure of the compound was verified by nuclear magnetic resonance (NMR), infrared spectroscopy (IR) and mass spectroscopy (MS).

EXAMPLE II 3-hydroxy-2-methylbenzoate

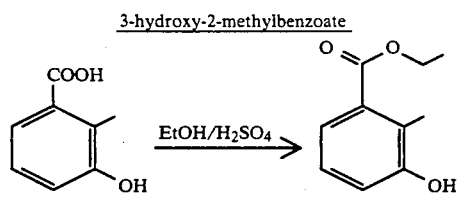

To a solution of the acid (8.0 g, 0.053 mol) in anhydrous ethanol (250 ml) was added the concentrated sulfuric acid (1.0 ml). The reaction mixture was allowed to heat at reflux for 20 hours and then cooled to room temperature. The ethanol was removed on the rotoevaporator and the residue was dissolved in EtOAc. The organic layer was washed sequentially with $H_2O$, aqueous saturated $NaHCO_3$ (2×), $H_2O$, dried ($MgSO_4$), filtered, and concentrated to a solid (5.6 g, 0.031 mol, 59%), m.p. 58°–60° C. The structure of the compound was verified by nuclear magnetic resonance (NMR), infrared spectroscopy (IR) and mass spectroscopy (MS).

EXAMPLE III 4-bromo-3-hydroxy-2-methylbenzoate

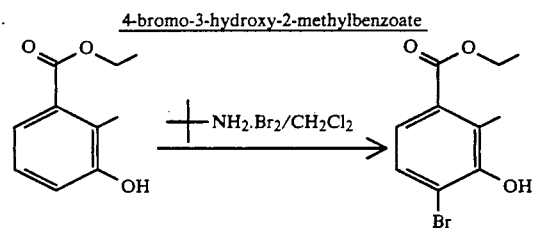

To a solution of the tert-butylamine (1.9 g, 0.026 mol) in $CH_2Cl_2$ (100 ml) at −78° C. was added a solution of bromine (4.08 g, 0.026 mol) in $CH_2Cl_2$ (30 ml) dropwise over 30 minutes. The mixture was stirred at −78° C. for another 30 minutes. A solution of the phenol (4.6 g, 0.026 mol) in $CH_2Cl_2$ (30 ml) was then added dropwise over 30 minutes. The reaction mixture was allowed to warm to room temperature and stir for 18 hours. Aqueous work-up followed by flash column chromatography purification (silica, 5.5:; Hexanes:$Et_2O$) yielded the product as a yellow oil (2.8 g, 42%). The structure of the compound was verified by nuclear magnetic resonance (NMR), infrared spectroscopy (IR) and mass spectroscopy (MS).

EXAMPLE IV 4-bromo-3-ethoxy-2-methylbenzoate

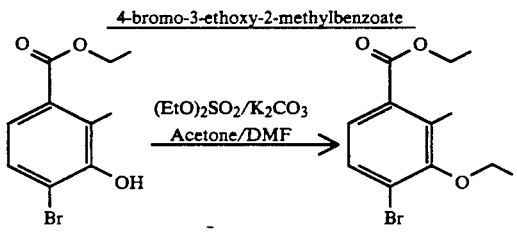

A mixture of the phenol (2.6 g, 0.01 mol), diethyl sulfate (1.7 g, 0.011 mol), and ($K_2CO_3$ (1.52 g, 0.011 mol) in acetone/DMF (20 ml/20 ml) was heated at reflux for 50 minutes then allowed to cool to room temperature and stir over night. The reaction mixture was filtered and the solvent acetone was removed on the rotoevaporator. The residue was poured onto ice/$H_2O$. The organic material was extracted into hexanes (2×). The combined hexanes layers were dried ($MgSO_4$), filtered, and concentrated to an oil (3.0 g, 0.01 mol, 100%). The structure of the compound was verified by nuclear magnetic resonance (NMR), infrared spectroscopy (IR) and mass spectroscopy (MS).

EXAMPLE V 3-ethoxy-2-methyl-4-methylthiobenzoate

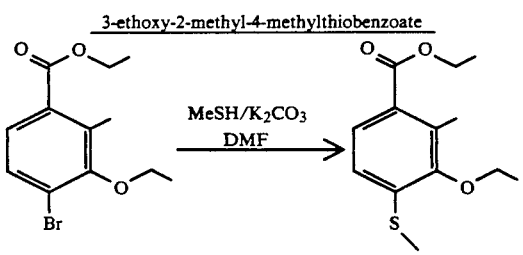

Methane thiol (1.5 g, 0.03 mol) was condensed into a stirred mixture of the bromo starting material (2.8 g, 0.01 mol), $K_2CO_3$ (2.07 g, 0.015 mol) in DMF (30 ml) at 0° C. The reaction vessel was rinsed with acetone (10 ml). The mixture was stirred at room temperature over night then heated at reflux for 6 hours. Gas chromatography analysis indicated 54% completion. The mixture was again cooled to 0° C. and more $CH_3SH$ (2.5 g, 0.05 mol) was condensed in and more $K_2CO_3$ (4.6 g, 0.033 mol) was added. The mixture was again brought to reflux for 6 hours. After cooling to room temperature, the reaction mixture was poured into ice cold aqueous 1N HCl. The organic materials were extracted into $Et_2O$ (2×). The combined organic layers were washed with 1N HCl, 5% $K_2CO_3$ (2×), dried ($MgSO_4$), filtered, and concentrated to an oil (2.25 g, 0.009 mol, 90%). The structure of the compound was verified by nuclear magnetic resonance (NMR), infrared spectroscopy (IR) and mass spectroscopy (MS).

EXAMPLE VI 3-ethoxy-2-methyl-4-methylthiobenzoic acid

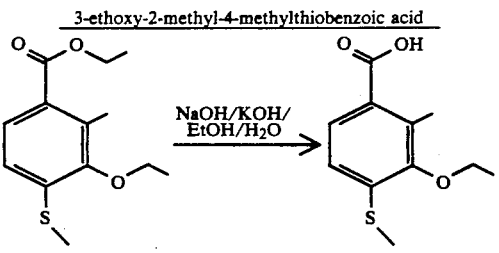

To a solution of the ester (2.2 g, 0.009 mol) in THF (20 ml) was added $H_2O$ (20 ml) followed by solid NaOH (1.7 g, 0.043 mol). The mixture was stirred at room temperature for 2 hours then at reflux for another 2 hours. KOH (2.4 g, 043 mol) and ethanol (5 ml) were added and the mixture was heated at reflux for 20 hours. The mixture, upon cooling to room temperature, was poured into a separatory funnel (the flask was rinsed with $Et_2O$). The layers were separated and the organic layer was extracted with aqueous 5% $K_2CO_3$. The combined basic layers were acidified at low temperature with concentrated HCl and the desired acid was extracted into EtOAc. The EtOAc layer was dried (MgSO4), filtered, and concentrated to an off white solid (2.2 g, 100%) m.p. 193°–196° C. The structure of the compound was verified by nuclear magnetic resonance (NMR), infrared spectroscopy (IR) and mass spectroscopy (MS).

EXAMPLE VII 3-ethoxy-2-methyl-4-methylsulfonylbenzoic acid

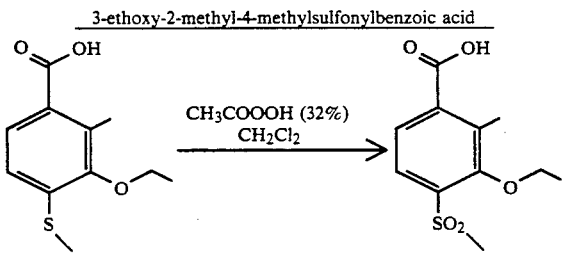

To a suspension of the acid (2.2 g, 0.01 mol) in CH2Cl2 (50 ml) at 0° C. was added the solution of 32% peracetic acid (4.6 ml, 0.022 mol) slowly. The solid went into solution and the mixture was allowed to warm to room temperature and stir for 3 days. More peracetic acid (1 ml) was added and the mixture was heated at reflux for 20 hours. The mixture was poured into a separatory funnel and the CH2Cl2 layer was washed once with H2O. The H2 layer was backextracted with CH2Cl2. The combined organic layers were dried (MgSO4), filtered, and concentrated to a white solid (2.3 g, 90%) m.p. 132°–136° C. The structure of the compound was verified by nuclear magnetic resonance (NMR), infrared spectroscopy (IR) and mass spectroscopy (MS).

EXAMPLE VIII

Ethyl 2-methyl-3-hydroxy-4-nitrobenzoate

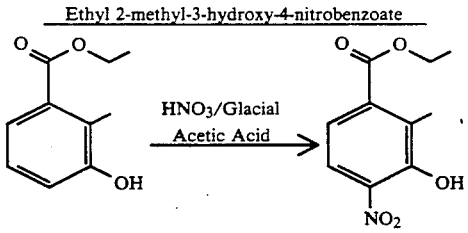

To a solution of the phenol (0.5 g, 0.0028 mol) in glacial acetic acid was added the ice (10 g) followed by concentrated nitric acid (specific gravity 1.42; 0.2 ml, 0.003 mol). The mixture was then stirred at room temperature for 45 minutes and another portion of nitric acid (0.2 ml, 0.003 mol) was added. Stirring was continued for one hour and excess ice was added to the reaction mixture. A yellow solid precipitated and was collected by suction filtration. Air-drying yielded the desired nitrated phenol (0.3 g, 48%). The structure of the compound was verified by nuclear magnetic resonance (NMR), infrared spectroscopy (IR) and mass spectroscopy (MS).

EXAMPLE IX

4-Bromo-2-methyl-3-(2-methyoxyethoxy)benzoic acid

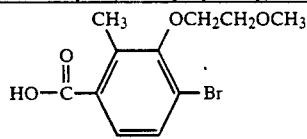

A mixture of ethyl 4-bromo-2-methyl-3-(2-methoxyethoxy)benzoate (6.6 grams (g), 0.02 mol), potassium oxide (5.9 g, 0.105 mol), and sodium hydroxide (4.2 g, 0.105 mol) in tetrahydrofuran (5 ml), ethanol (5 ml), and water (100 ml) was heated at reflux for 3 hours. Upon cooling to room temperature, the reaction vessel was chilled in an ice/water bath. The content was acidified to pH with <1 with concentrated hydrochloric acid and extracted with diethyl ether. The organic layer was dried (magnesium sulfate), filtered, and concentrated in vacuo to afford the desired free acid (5.8 g, 95% yield) as a slightly yellow solid.

The above-described benzoic acid was converted to its acid chlorides using oxalyl chloride and a catalytic amount of dimethylformamide. The acid chloride was reacted with the appropriately substituted dione to prepare the below-described herbicidal 2,3,4-trisubstituted benzoyl-1,3-cyclohexanediones according to the two-step reaction previously described.

The following example teaches the synthesis of a representative 2-(2',3',4'-trisubstituted)-1,3-cyclohexane-dione compound of this invention.

EXAMPLE X

2-[4'-Bromo-2'-methyl-3'-(2-methoxyethoxy)
benzoyl]-5-methyl-1,3-cyclohexanedione

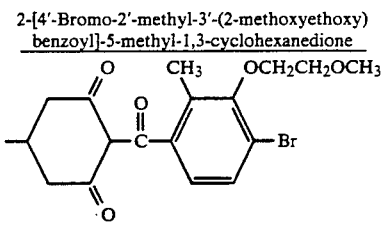

4-Bromo-2-methyl-3-(2-methoxyethoxy)benzoic acid (1.5g, 0.0052 mol) was diluted in methylene chloride (30 ml) and dimethyl formamide (5 drops) was added, followed by the slow addition of oxalyl chloride (2.0 g, 0.0156 mol) at 0° C. After the addition was complete, the reaction mixture was heated at reflux for 2 hours, cooled and concentrated under vacuum. The crude acid chloride was dissolved in methylene chloride (10 ml) and the solution was added slowly to a mixture of 5-methyl-1,3-cyclohexanedione (0.72 g, 0.0057 mol) and triethylamine (1.6 g, 0.0156 mol) in acetonitrile (30 ml) at 0° C. The reaction mixture was allowed to stir at room temperature for 3 hours and acetocyanohydrin (10 drops) was added. Stirring was continued overnight. The solvents were removed in vacuo and diethylether was added to the residue. The organic layer was washed with aqueous 1 normal(N) hydrochloric acid (2 times). The acidic materials were extracted into aqueous 5% potassium carbonate (3 times). The combined basic layers were acidified to pH 6 (at 0° C.) with concentrated hydrochloric acid and the desired product was extracted into methylene chloride (2 times). Further purification as a copper (II) chelate yielded the desired compound 1.1 g, 53% yield) as a light yellow oil.

The following is a table of certain selected compounds that are preparable according to the procedure described hereto. Compound numbers are assigned to each compound and are used throughout the remainder of the application.

TABLE 14

$R^2$ $R^1$ O CH$_3$
$R^3$ — — $\|$ — OCH$_2$CH$_2$OR$^7$
$R^4$ — — C — — $R^8$
$R^5$ $R^6$ O

| Compd. No. | R$^1$ | R$^2$ | R$^3$ | R$^4$ | R$^5$ | R$^6$ | R$^7$ | R$^8$ | m.p. °C. |
|---|---|---|---|---|---|---|---|---|---|
| 1[a] | H | H | CH$_3$ | H | H | H | CH$_3$ | Br | oil |
| 2 | H | H | H | H | H | H | CH$_3$ | Br | oil |

[a] Prepared in Example X.

HERBICIDAL SCREENING TESTS

As previously mentioned, the herein described compounds produced in the above-described manner are phytotoxic compounds which are useful and valuable in controlling various plant species. Selected compounds of this invention were tested as herbicides in the following manner.

Pre-emergence Multi-weed Herbicide Test: On the day preceding treatment, seeds of eight different weed species are planted in loamy sand soil in individual rows using one species per row across the width of a flat. The weeds used are pigweed (PW (*Amaranthus retroflexus*), giant foxtail (GFT) (*Setenia faberi*), green foxtail (FT (*Setaria viridis*), watergrass (WG) (*Echinochloa crusoalli*), broadleaf signalgrass (BSG) (*Brachiaria platyphylla*), annual morning-glory (AMG) (*Ipomoea lacunosa*), velvetleaf (VL) (*Abutilon theoohrasti*), and cocklebur (CB) (*Xanthium sp.*). Ample seeds are planted to give about 20 to 40 seedlings per row, after emergence, depending upon the size of the plants.

Using an analytical balance, 37.5 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 40 gallons per acre (748 L/ha). The application rate if /14 lb/acre (0.28 Kg/ha).

After treatment, the flats are placed in the greenhouse at a temperature of 70° to 80° F and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the test are shown in the following Table 15.

TABLE 15

Pre-emergence Herbicidal Activity
Application Rate - 0.25 lb/A

| Compd. No. | FT | GFT | WG | BSG | AMG | VL | PW | CB |
|---|---|---|---|---|---|---|---|---|
| 1 | 10 | 20 | 100 | 100 | 40 | 100 | 20 | 100 |
| 2 | 100 | 100 | 100 | 100 | 15 | 100 | 95 | 100 |

Post-emergence Multi-weed Herbicide Test: This test is conducted in an identical manner to the testing procedure for the pre-emergence multi-weed herbicide test, except the seeds of the twelve different weed species are planted 10-12 days before treatment. Also, watering of the treated flats is confined to the soil surface and not to the foliage of the sprouted plants.

Post-emergence Multi-weed Herbicide Test: This test is conducted in an identical manner to the testing procedure for the post-emergence herbicide test, except the seeds of the twelve weed species used in the pre-emergence multi-weed herbicide test were used and the seeds were planted 10-12 days before treatment. Also, watering of the treated flats is confined to the soil surface and not to the foliage of the sprouted plants.

The results of the post-emergence multi-weed herbicide test are reported in Table 16.

TABLE 16

Post-emergence Multi-weed Herbicidal Activity
Application Rate - 0.28 kg/ha

| Compd. No. | FT | GFT | WG | BSG | AMG | VL | PW | CB |
|---|---|---|---|---|---|---|---|---|
| 1 | 10 | 100 | 100 | 100 | 100 | 100 | 100 | 100 |
| 2 | 100 | 100 | 100 | 100 | 100 | 100 | 100 | 100 |

The compounds of the present invention are useful as herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 10 pounds per acre, preferably from about 0.1 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal compositions.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

| EMULSIFIABLE CONCENTRATE FORMULATIONS | | | |
|---|---|---|---|
| General Formula with Ranges | | Specific Formula | |
| herbicidal compound | 5–55 | herbicidal compound | 54 |
| surfactant(s) | 5–25 | proprietary blend of oil-soluble | 10 |
| solvent(s) | 20–90 | sulfonates and polyoxyethylene ethers | |
| | 100% | polar solvent | 27 |
| | | petroleum hydrocarbon | 9 |
| | | | 100% |
| WETTABLE POWDER FORMULATIONS | | | |
| herbicidal compound | 3–90 | herbicidal compound | 80 |
| wetting agent | 0.5–2 | sodium dialkyl | 0.5 |
| dispersing agent | 1–8 | naphthalene sulfonate | |
| diluent(s) | 8.5–87 | sodium lignosulfonate | 7 |
| | 100%. | attapulgite clay | 12.5 |
| | | | 100% |
| EXTRUDED GRANULAR FORMULATIONS | | | |
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| antifreeze agent | 1–10 | propylene glycol | 10 |

| | | | | |
|---|---|---|---|---|
| antimicrobial agent | 1–10 | BIT | | 0.03 |
| antifoam agent | 0.1–1 | silicone defoamer | | 0.02 |
| solvent | 7.95–76.85 | water | | 39.9 |
| | 100% | | | 100% |

When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

The herbicidal compounds of this invention can be used in combination with other herbicidal compounds for broader spectrum control of undesirable vegetation. Examples of other herbicidal compounds are as follows:

1. Anilides

Alachlor - 2-chloro-2′,6′-diethyl-N-(methoxymethyl) acetanilide Metolachlor - 2-chloro-2′-methyl-6′ethyl-N-methoxy-isopropyl-2-acetanilide Propanil - N-(3,4-dichlorophenyl-)propionanilide Acetachlor - 2-chloro-2′-methyl-6′ethyl-N-ethoxymethyl-acetanilide

2. Triazines

Atrazine - 2-chloro-4-(ethylamino)-6-isopropylamino)-s-triazine Cyanazine - 2-chloro-4-(1-cyano-1-methylethylamino)-6-ethylamino-s-triazine Metribuzin - 4-amino-6 -tert-butyl-3-(methylthio)-1,2,4-triazin-5(4H)-one

3. Thiocarbamates

Molinate - S-ethyl hexahydro-1H-azepine-1-carbothioate Butylate - S-ethyl diisobutylthiocarbamate

4. Ureas

Monuron - 3-(p-chlorophenyl)-1,1-dimethylurea
Linuron - 3-(3,4-dichlorophenyl)-1-methoxy-1-methylurea

5. Toluidines

Trifluralin - α,α,α-trifluoro-2,6-dinitro-N,N-dipropyl-p-toluidine Pendimethalin - N-(1-ethylpropyl)-3,4-dimethyl-2,6-dinitro-benzeneamine

6. Hormones 2,4-D - (2,4-dichlorophnoexy) acetic acid MCPA - (2-methyl-4-chlorophenoxy) acetic acid

7. Diazines

Bentazon - 3-isopropyl-1H-2,3,1-benzothiadiazin-4(3H)-one 2,2-dioxide Oxadiazon - 2-tert-butyl-4-(2,4-dichloro-5-isopropoxy-phenyl)-Δ²-1,3,4-oxadiazolin-5-one

8. Diphenyl ethers

Acifluorfen - sodium 5-[2-chloro-4-(trifluoromethyl)-phenoxy]-2-nitrobenzoate Fluazifop-butyl -(±)-butyl 2[4](5-(trifluoromethyl)-2-pyridinyl)oxy]phenoxy propanoate Chlomethoxynil - 2,4-dichlorophenyl 3-methoxy-4-nitro-phenyl ether

9. Imidazolinones

Imazaquin - 2-[4,5-dihydro-4-methyl-4-(1-methylethyl)-5-oxo-1H-imidazol-2-yl]-3quinolin carboxylic acid

10. Sulfonyl ureas

Bensulfuron methyl - methyl 2-[[[[[(4,6-dimethoxypyrimidin-2-yl)amino]carbonyl]amino]sulfonyl]methyl]benzoate Chlorimuron ethyl - ethyl 2-(((((4-chloro-6-methoxypyr-imidin-2-yl)amino)carbonyl)amino)sulfonyl) benzoate

11. 2-(2-Substituted benzoyl)-1,3-cyclohexanediones 2- (2′-chloro-4-methysulfonyl benzoyl)-1,3-cyclohexanedione

12. Miscellaneous compounds

Dimethazone - 2-(2-chlorophenyl)methyl-4,4-dimethyl-3-isoxazolidinone Norflurazon - 4-chloro-5-(methylamino)-2-α,α, α, -trifluoro-m-tolyl)-3-(2H)-pyridazinone Dalapon - 2,2-dichloropropionic acid Glyphosate - isopropyl amine salt of N-(phosphonomethyl) glycine Fenoxaprop-ethyl - (+)-ethyl-2,4-((6-chloro-2-benzoxazoly loxy)phenoxy)propanoate

WHAT IS CLAIMED IS:

1. A compound having the structural formula

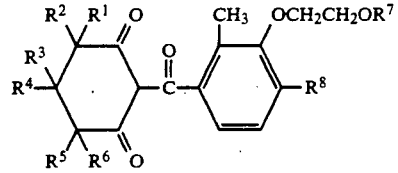

wherein
$R^1$ is hydrogen or $C_1$–$C_4$ alkyl;
$R^2$ is hydrogen or $C_1$–$C_4$ alkyl;
$R^3$ is hydrogen or $C_1$–$C_4$ alkyl;
$R^4$ is hydroxy, hydrogen or $C_1$–$C_4$ alkyl; or
$R^3$ and $R^4$ together are carbonyl (=O) with the proviso that $R^1$, $R^2$, $R^5$ and $R^6$ are $C_1$–$C_4$ alkyl;
$R^5$ is hydrogen or $C_1$–$C_4$ alkyl;
$R^6$ is hydrogen, $C_1$–$C_4$ alkyl, $C_1$–$C_4$ alkylthio, or $C_1$–$C_4$ alkylsulfonyl, with the proviso that when $R^6$ is $C_1$–$C_4$ alkylthio or $C_1$–$C_4$ alkylsulfonyl, then $R_3$ and $R^4$ are not together carbonyl;
$R^7$ is methyl or ethyl; and
$R^8$ is (1) halogen; (2) nitro; or (3) $R^bSO_n$- wherein n is the integer 0 or 2, and $R^b$ is (a) $C_1$–$C_4$ alkyl; and its salts.

2. A compound of claim 1 wherein $R^1$ is hydrogen or methyl; $R^2$ is hydrogen or methyl; $R^3$ is hydrogen or methyl; $R^4$ is hydrogen or methyl or $R^3$ and $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methylsulfonyl with the proviso that when $R^6$ is methylthio or methylsulfonyl, then $R^3$ and $R^4$ are not together carbonyl; $R^7$ is methyl or ethyl; is chlorine, bromine, nitro or $R^bSO_2$ wherein $R^b$ is $C_1$–$C_2$ alkyl.

3. The compound of claim 2 wherein $R^1$ is hydrogen, $R^2$ is hydrogen, $R_3$ is methyl, $R^4$ is hydrogen, $R^5$ is hydrogen, $R^6$ is hydrogen, $R^7$ is methyl and is bromine.

4. The compound of claim 2 wherein $R^1$ is hydrogen, $R^2$ is hydrogen, $R^3$ is hydrogen, $R^4$ is hydrogen, $R^5$ is hydrogen $R^6$ is hydrogen, $R^7$ is methyl and is bromine.

5. The method of controlling undesirable vegetation comprising applying to the area where control is desired, an herbicidally effective amount of a compound having the structural formula

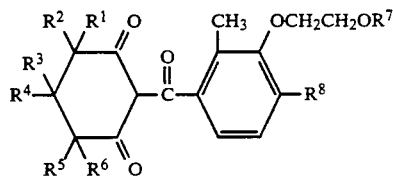

wherein
$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R_4$ is hydrogen is hydroxy, hydrogen or $C_1$-$C_4$ alkyl; or
$R^3$ and $R^4$ together are carbonyl (=O) with the proviso that $R^1$, $R^2$, $R^5$ and $R^6$ are $C_1$-$C_4$ alkyl;
$R^5$ is hydrogen or $C_1$-$C_4$ alkyl;
$R^6$ is hydrogen, $C_1$-$C_4$ alkyl, $C_1$-$C_4$ alkylthio, or $C_1$-$C_4$ alkylsulfonyl, with the proviso that when $R^6$ is $C_1$-$C_4$ alkylthio or $C_1$-$C_4$ alkylsulfonyl, then $R_3$ and $R^4$ are not together carbonyl;
$R^7$ is methyl or ethyl; and
$R^8$ is (1) halogen; (2) nitro; or (3) $R^bSO_n$-wherein n is the integer 0 or 2, and $R^b$ is (a) $C_1$-$C_4$ alkyl; and its salts.

6. The method of claim 5 wherein $R^1$ is hydrogen or methyl; $R^2$ is hydrogen or methyl; $R^3$ is hydrogen or methyl; $R^4$ is hydrogen or methyl or $R^3$ and $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methylsulfonyl with the proviso that when $R^6$ is methylthio or methylsulfonyl, then $R^3$ and $R^4$ are not together carbonyl; $R^7$ is methyl or ethyl; $R^8$ is chlorine, bromine, nitro or $R^bSO_2$ wherein $R^b$ is $C_1$-$C_2$ alkyl.

7. The method of claim 6 wherein $R^1$ is hydrogen, $R^2$ is hydrogen, $R^3$ is methyl, $R^4$ is hydrogen, $R^5$ is hydrogen, $R^6$ is hydrogen, $R^7$ is methyl and $R^8$ is bromine.

8. The method of claim 6 wherein $R^1$ is hydrogen, $R^2$ is hydrogen, $R^3$ is hydrogen, $R^4$ is hydrogen, $R^5$ is hydrogen, $R^6$ is hydrogen, $R^7$ is methyl and $R^8$ is bromine.

9. A herbicidal composition comprising an herbicidally effective amount of a compound having the structural formula

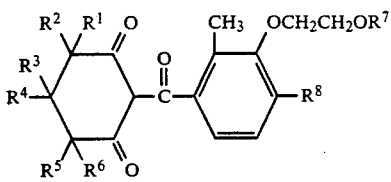

wherein
$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R^4$ is hydroxy, hydrogen or $C_1$-$C_4$ alkyl; or
$R^3$ and $R^4$ together are carbonyl (=O) with the proviso that $R^1$, $R^2$, $R^5$ and $R^6$ are $C_1$-$C_4$ alkyl;
$R^5$ is hydrogen or $C_1$-$C_4$ alkyl;
$R^6$ is hydrogen, $C_1$-$C_4$ alkyl, $C_1$-$C_4$ alkylthio, or $C_1$-$C_4$ alkylsulfonyl, with the proviso that when $R^6$ is $C_1$-$C_4$ alkylthio or $C_1$-$C_4$ alkylsulfonyl, then $R_3$ and $R^4$ are not together carbonyl;
$R^7$ is methyl or ethyl; and
$R^8$ is (1) halogen; (2) nitro; or (3) $R^bSO_n$— wherein n is the integer 0 to 2, and $R^b$ is (a) $C_1$-$C_4$ alkyl; and its salts.

10. The herbicidal composition of claim 9 wherein $R^1$ is hydrogen or methyl; $R^2$ is hydrogen or methyl; $R^3$ is hydrogen or methyl; $R^4$ is hydrogen or methyl or $R^3$ and $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methylsulfonyl with the provisio that when $R^6$ is methylthio or methylsulfonyl, then $R^3$ and $R^4$ are not together carbonyl; $R^7$ is methyl or ethyl; $R^8$ is chlorine, bromine, nitro or $R^bSO_2$ wherein $R^b$ is $C_1$-$C_2$ alkyl.

11. The herbicidal composition of claim 10 wherein $R^1$ is hydrogen, $R^2$ is hydrogen, $R^3$ is methyl, $R^4$ is hydrogen, $R^5$ is hydrogen, $R^6$ is hydrogen, $R^7$ is methyl and $R^8$ is bromine.

12. The herbicidal composition of claim 10 wherein $R^1$ is hydrogen, $R^2$ is hydrogen, $R^3$ is hydrogen, $R^4$ is hydrogen, $R^5$ is hydrogen, $R^6$ is hydrogen, $R^7$ is methyl and $R^8$ is bromine.

* * * * *